US007919762B2

(12) United States Patent
Trupke et al.

(10) Patent No.: US 7,919,762 B2
(45) Date of Patent: Apr. 5, 2011

(54) DETERMINING DIFFUSION LENGTH OF MINORITY CARRIERS USING LUMINESCENCE

(75) Inventors: Thorsten Trupke, Coogee (AU); Robert Andrew Bardos, Bronte (AU); Peter Wilhelm Wurfel, Karlsruhe (DE)

(73) Assignee: BT Imaging Pty Ltd, Sydney, New South Wales ( * ) Notice: Subject to any disclaimer, the term of this patent is extended or adjusted under 35 U.S.C. 154(b) by 45 days.

(21) Appl. No.: 12/375,889

(22) PCT Filed: Jul. 27, 2007

(86) PCT No.: PCT/AU2007/001050
§ 371 (c)(1),
(2), (4) Date: Sep. 1, 2009

(87) PCT Pub. No.: WO2008/014537
PCT Pub. Date: Feb. 7, 2008

(65) Prior Publication Data
US 2010/0025588 A1   Feb. 4, 2010

(30) Foreign Application Priority Data

Aug. 1, 2006   (AU) .............................. 2006904160

(51) Int. Cl.
*G01N 21/64* (2006.01)
(52) U.S. Cl. .................. 250/459.1; 250/362; 250/458.1
(58) Field of Classification Search .................. 250/362, 250/458.1, 459.1
See application file for complete search history.

(56) References Cited

U.S. PATENT DOCUMENTS

| 4,273,421 A | 6/1981 | Gurtler |
| 5,202,744 A * | 4/1993 | Louis ............................... 356/73 |
| 6,512,384 B1 | 1/2003 | Lagowski et al. |

(Continued)

FOREIGN PATENT DOCUMENTS

EP   0 545 523 A2   6/1993

(Continued)

OTHER PUBLICATIONS

Wang, Chin Hsin et al., Minority-Carrier Lifetime & Surface Recombination Velocity Measurement by Frequency-Domain Photoluminescence, IEEE Transactions on Electron Devices, vol. 38, No. 9, Sep. 1991, pp. 2169-2180.

(Continued)

*Primary Examiner* — David P Porta
*Assistant Examiner* — Marcus H Taningco
(74) *Attorney, Agent, or Firm* — Fish & Richardson P.C.

(57) ABSTRACT

Methods (200, 300), apparatuses and systems (100) for determining minority carrier diffusion lengths in a semi-conductor structure (130), which may be a solar cell or a unprocessed or partially processed silicon sample, are disclosed. The luminescence (140) may comprise photoluminescence, electroluminescence, or both. Luminescence (140) is excited (212) in the structure (130), and the intensities of short- and long-wavelength luminescence (140) are measured (214). Luminescence intensities may be captured from either side of the sample using a single photodetector, a FPA, a CCD array (150), or a mapping tool. The luminescence (140) excited in the structure (130) may be filtered (160) at short and long cutoff wavelengths. Diffusion lengths of the structure (130) are generated (216) using a predefined theoretical relationship. The generating step (216) may comprise calculating (316) intensity ratios from luminescence intensities and converting (320) the intensity ratios into diffusion lengths using the predefined theoretical relationship.

18 Claims, 4 Drawing Sheets

U.S. PATENT DOCUMENTS

| | | | |
|---|---|---|---|
| 7,026,831 B2 * | 4/2006 | Hermes | 324/754.23 |
| 7,113,276 B1 * | 9/2006 | Higgs et al. | 356/318 |
| 2003/0094579 A1 * | 5/2003 | Hasegawa et al. | 250/458.1 |
| 2005/0206402 A1 | 9/2005 | Shi et al. | |

FOREIGN PATENT DOCUMENTS

| | | |
|---|---|---|
| JP | 10-135291 | 5/1998 |
| WO | WO 02/03053 | 1/2002 |

OTHER PUBLICATIONS

Supplementary European Search Report dated Dec. 28, 2009 for corresponding application EP 07784695.

Kaneta A. et al., "Near-field Photoluminescence Study in Violet Light Emitting InGaN Single Quantum Well Structures", Phys. Stat. Sol. (c) 2, No. 7, pp. 2728-2731(2005)/DOI 10.1002/pssc.200461580.

International Search Report dated Oct. 3, 2007, for corresponding PCT application PCT/AU2007/001050.

Tarasov et al., "Defect Passivation in Multicrystalline Silicon for Solor Cells" *Appl. Phys. Ltr.*, 85 (19): 4346-4348 (2004).

Ostapenko and Romero, "Defect Mapping in Full-Size Multi-Crystalline Si Wafers" *Eur. Phys. J. Appl. Phys.*, 27: 55-58 (2004).

Ostapenko et al., "Defect Monitoring Using Scanning Photoluminescence Spectroscopy in Multicrystalline Silicon Wafers" *Semicond. Sci. Technol.*, 15: 840-848 (2000).

* cited by examiner

DETERMINING DIFFUSION LENGTH OF MINORITY CARRIERS USING LUMINESCENCE

TECHNICAL FIELD

The present invention relates generally to semiconductors and in particular to methods of determining minority-carrier diffusion length in semiconductor structures.

BACKGROUND

Multi-wavelength Light Beam Induced Charge (LBIC) mapping of diffusion length is a known technique for determining minority-carrier diffusion length. However, the technique's slow speed and restriction to finished solar cells (wafers cannot be measured) are some of its main limitations.

Images of minority carrier effective lifetime in silicon wafers can be obtained using the techniques of Carrier Density Imaging (CDI) or Infrared Lifetime mapping (ILM). The conversion of images of minority carrier effective lifetime obtained with these methods into images of diffusion length requires additional knowledge of the silicon wafer, for example, the spatially dependant carrier mobility and the spatially dependant surface recombination velocity. A significant limitation of these techniques is that such techniques cannot be applied to finished solar cells with a full rear metallization, because the techniques are based on infrared free carrier emission or infrared free carrier absorption, measured against a cold or heated background, respectively. Thus, these techniques are ruled out for industrial screen printed solar cells. In addition, CDI and ILM are affected by artifacts resulting from excess carriers in space charge regions and by artifacts resulting from minority carrier trapping.

Electroluminescence images of solar cells have been used by Takashi Fuyuki's group to get diffusion length images: Fuyuki, T., H. Kondo, T. Yamazaki, Y. Takahashi and Y. Uraoka, "Photographic surveying of minority carrier diffusion length in polycrystalline silicon solar cells by electroluminescence", Applied Physics Letters, 2005, 86(26), p. 262108. This technique is limited to finished cells. The measured photon count per pixel is assumed to be linear in the diffusion length. A separate calibration is required to obtain a linearity factor that converts counts per pixel into diffusion lengths. Also, the influence of photon reabsorption and of resistive losses due to lateral current flow is neglected in this simplified analysis, effects that can lead to significant experimental artifacts.

Thus, a need clearly exists for improved methods and systems for determining the diffusion length of minority carriers in semiconductor structures.

SUMMARY

In accordance with an aspect of the invention, there is provided a method of determining minority carrier diffusion lengths in a semiconductor structure. Luminescence is excited in the semiconductor structure. Intensities of short-wavelength and long-wavelength luminescence are measured. The measurements at short wavelengths and long wavelengths are made in different spectral intervals with a spectral centre of mass that is at a shorter wavelength in one measurement than in the other measurement; the long wavelength is greater than the short wavelength. Diffusion lengths of the semiconductor structure are generated dependent upon the measured intensities of the short-wavelength and long-wavelength luminescence using a predefined theoretical relationship.

The intensities of luminescence may be measured, and the diffusion lengths are generated as a spatially averaged quantity using a single detector, or on a pixel-by-pixel basis, or by binning. The measuring step may comprise the step of capturing images of the luminescence emitted by the semiconductor structure. The images may be captured using a Focal Plane Array (FPA), a CCD array, or a mapping tool.

The measuring step may comprise capturing the luminescence intensity over a spectral interval using a photodetector. The photodetector may comprise a photodiode.

The method may further comprise the step of filtering at short and long cutoff wavelengths the luminescence excited in the semiconductor structure; the long cutoff wavelength is greater than the short cutoff wavelength. Filtering may be applied before the capturing step. Alternatively, the filtering may be applied after capturing the images and may be implemented using computer software.

The filtering may be implemented using different filters with different cut off wavelengths, or alternatively using at least two short-pass filters, one with a longer cutoff wavelength than the other.

The filtering may be implemented using one short-pass filter, or using a long-pass filter, where the long-pass filtered integrated luminescence intensity is subtracted from the total spectrum of luminescence.

The generating step may comprise the substep of calculating intensity ratios from captured luminescence intensities.

The generating step may comprises the substep of converting the intensity ratios into diffusion lengths using a predefined theoretical relationship dependent upon characteristics of at least one filter, spectral sensitivity of a sensor and surface recombination velocities of the semiconductor structure. The method may further comprise the step of calculating the theoretical relationship between the intensity ratios and the diffusion lengths. The theoretical relationship may be defined as follows:

$$\frac{d j_{y,detect}}{d\hbar\omega}(\hbar\omega) = T_{filter}(\hbar\omega) \cdot S_{Capture}(\hbar\omega) \cdot \frac{d j_{y,em}}{d\hbar\omega}(\hbar\omega)$$

where $S_{capture}$ is the luminescence capture device's sensitivity, $T_{filter}$ is the transmission of a respective filter, $dj_{y,em}(\hbar\omega)$ is the photon current emitted through a surface in the energy interval $d\hbar\omega$, the quantity $dj_{y,em}(\hbar\omega)$ is dependent upon a specific value of diffusion length and a specific value of surface recombination velocities.

The generating step may comprise the substep of dividing the measured intensities on a pixel-by-pixel basis.

The method may further comprise the step of generating an image displaying the variation of diffusion length over the semiconductor structure.

The semiconductor structure may be a bare wafer, or a partially or fully fabricated solar cell.

The luminescence may be photoluminescence, electroluminescence, or both.

In accordance with another aspect of the invention, there is provided an apparatus for determining minority carrier diffusion lengths in a semiconductor structure. The apparatus comprising: a mechanism for exciting luminescence in the semiconductor structure; a mechanism for measuring intensities of short-wavelength and long-wavelength luminescence, the measurements at short wavelengths and long wavelengths being made in different spectral intervals with a spectral centre of mass that is at a shorter wavelength in one measurement than in the other measurement, the long wavelength being greater than the short wavelength; and a mechanism for generating diffusion lengths of the semiconductor structure dependent upon the measured intensities of the short-wavelength and long-wavelength luminescence using a predefined theoretical relationship.

The intensities of luminescence may be measured and the diffusion lengths may be generated as a spatially averaged quantity using a single detector, or on a pixel-by-pixel basis, or by binning.

The measuring mechanism comprises a mechanism for capturing images of the luminescence emitted by the semiconductor structure. The image capturing mechanism may comprise a Focal Plane Array (FPA), a CCD array, or a mapping tool.

The measuring mechanism may comprise a photodetector for capturing the luminescence intensity over a spectral interval. The photodetector may comprise a photodiode.

The apparatus further comprising a mechanism for filtering at short and long cutoff wavelengths the luminescence excited in the semiconductor structure, the long cutoff wavelength being greater than the short cutoff wavelength. The filtering may be applied before capturing the luminescence, or after capturing the images. If after capturing, the filtering may be implemented using computer software.

The filtering may be implemented using different filters with different cut off wavelengths.

The apparatus may comprise at least two short-pass filters, one with a longer cutoff wavelength than the other, to implement the filtering.

The filtering may be implemented using one short-pass filter.

The apparatus may further comprise a long-pass filter to implement the filtering, where the long-pass filtered integrated luminescence intensity is subtracted from the total spectrum of luminescence.

The generating mechanism may comprise a mechanism for calculating intensity ratios from captured luminescence intensities.

The generating mechanism may comprise a mechanism for converting the intensity ratios into diffusion lengths using a predefined theoretical relationship dependent upon characteristics of at least one filter, spectral sensitivity of a sensor and surface recombination velocities of the semiconductor structure. The apparatus may further comprising a mechanism for calculating the theoretical relationship between the intensity ratios and the diffusion lengths. The theoretical relationship may be defined as follows:

$$\frac{d j_{y,detect}}{d\hbar\omega}(\hbar\omega) = T_{filter}(\hbar\omega) \cdot S_{Capture}(\hbar\omega) \cdot \frac{d j_{y,em}}{d\hbar\omega}(\hbar\omega)$$

where $S_{Capture}$ is the camera's sensitivity, $T_{filter}$ is the transmission of a respective filter, $dj_{y,em}(\hbar\omega)$ is the photon current emitted through a surface in the energy interval $d\hbar\omega$, the quantity $dj_{y,em}(\hbar\omega)$ is dependent upon a specific value of diffusion length and a specific value of surface recombination velocities.

The generating mechanism may comprise a mechanism for dividing the measured intensities on a pixel-by-pixel basis.

The semiconductor structure may be a bare wafer, or a partially or fully fabricated solar cell.

The apparatus may further comprise a mechanism for generating an image displaying the variation of diffusion length over the semiconductor structure.

The luminescence may be photoluminescence, electroluminescence, or both.

In accordance with yet another aspect of the invention, there is provided a method for determining minority carrier diffusion length in a semiconductor structure. The method comprises: exciting the semiconductor structure to emit luminescence from the semiconductor structure, the luminescence comprising photoluminescence, electroluminescence, or both; filtering the luminescence excited in the semiconductor structure at short wavelengths and long wavelengths, each with a spectral centre of mass at a different spectral wavelength; capturing luminescence intensities from the semiconductor structure, each in a different spectral interval; and calculating intensity ratios from captured luminescence intensities dependent upon short-wavelength and long-wavelength intensities in different intervals from corresponding portions of the semiconductor structure, and converting the intensity ratios into diffusion lengths using a theoretical relationship dependent upon the filtering, spectral sensitivity of a sensor and surface recombination velocities of the semiconductor structure.

In accordance with still another aspect of the invention, there is provided a system for determining minority carrier diffusion length in a semiconductor structure. The system comprises: an excitation source for exciting the semiconductor structure to emit luminescence from the semiconductor structure, the luminescence comprising photoluminescence, electroluminescence, or both; at least one filter for filtering the luminescence excited in the semiconductor structure at short wavelengths and long wavelengths, each with a spectral centre of mass at a different spectral wavelength; and a luminescence capture device for capturing luminescence intensities emitted from the semiconductor structure, each in a different spectral interval; and a computing device for calculating intensity ratios from captured luminescence intensities dependent upon short-wavelength and long-wavelength intensities in different spectral intervals from corresponding portions of the semiconductor structure, and for converting the intensity ratios into diffusion lengths using a theoretical relationship dependent upon characteristics of the at least one filter, spectral sensitivity of a sensor and surface recombination velocities of the semiconductor structure.

The foregoing and further aspects of the invention are disclosed hereinafter.

BRIEF DESCRIPTION OF DRAWINGS

Embodiments of the invention are described hereinafter with reference to the drawings, in which.

DETAILED DESCRIPTION

Methods, apparatuses, and systems for determining minority carrier diffusion length in a semiconductor structure are described. In the following description, numerous specific details, including semiconductors, luminescence capture devices, semiconductor structures, particular filter cutoff wavelengths, and the like are set forth. However, from this disclosure, it will be apparent to those skilled in the art that modifications and/or substitutions may be made without departing from the scope and spirit of the invention. In other circumstances, specific details may be omitted so as not to obscure the invention.

Where reference is made in any one or more of the accompanying drawings to steps and/or features, which have the same or like reference numerals, those steps and/or features have for the purposes of this description the same function(s) or operation(s), unless the contrary intention appears.

In the context of this specification, the word "comprising" has an open-ended, non-exclusive meaning: "including principally, but not necessarily solely", but neither "consisting essentially of" nor "consisting only of". Variations of the word "comprising", such as "comprise" and "comprises", have corresponding meanings.

In the description hereinafter, the terms short wavelength measurement and long wavelength measurement are used. When reference is made to measurements at short wavelengths and long wavelengths, these terms have the meaning that two measurements are made in different spectral intervals with a spectral centre of mass that is at shorter wavelength in one measurement (referred to as short wavelength) than in the other measurement (referred to as long wavelength). These terms apply throughout the document unless the contrary is explicitly stated. For example if one measurement is carried out without filtering, thereby capturing the intensity integrated across the entire spectrum and the second measurement is carried out with a short pass filter, then the first measurement would be referred to as the long wavelength measurement and the second measurement would be described as the short wavelength measurement.

1. Introduction

The embodiments of the invention involve the determination of the diffusion length of minority carriers in semiconductor structures, including solar cells. This is an important parameter for the quality of solar cells. Methods in accordance with the embodiments of the invention make use of light emitted inside a solar cell or semiconductor sample by spontaneous radiative recombination of electron-hole pairs. The rate of spontaneous emission in a specific volume element is directly linked to the carrier densities of electrons and holes in that volume element. The spontaneously emitted light, which is emitted throughout the entire volume of the solar cell or sample according to the carrier distribution, may be reabsorbed before the same light reaches the surface of the solar cell.

The absorption coefficient of most solar cell materials (in particular semiconductors) increases with decreasing wavelength of the light over the spectral range, in which electroluminescence and photoluminescence occur. Thus, light with a shorter wavelength is more readily reabsorbed on the way to the surface than light with a longer wavelength. Therefore, the light (i.e. photoluminescence, or electroluminescence, or both) emitted through the surface of the semiconductor sample contains contributions from the entire volume of the semiconductor sample at long wavelengths, but contains contributions from close to the surface only at shorter wavelengths. The embodiments of the invention involve the comparison of the luminescence intensities (i.e. photoluminescence or electroluminescence or both) in different spectral intervals. The luminescence intensities in at least two different spectral intervals are measured separately.

Figure 1:
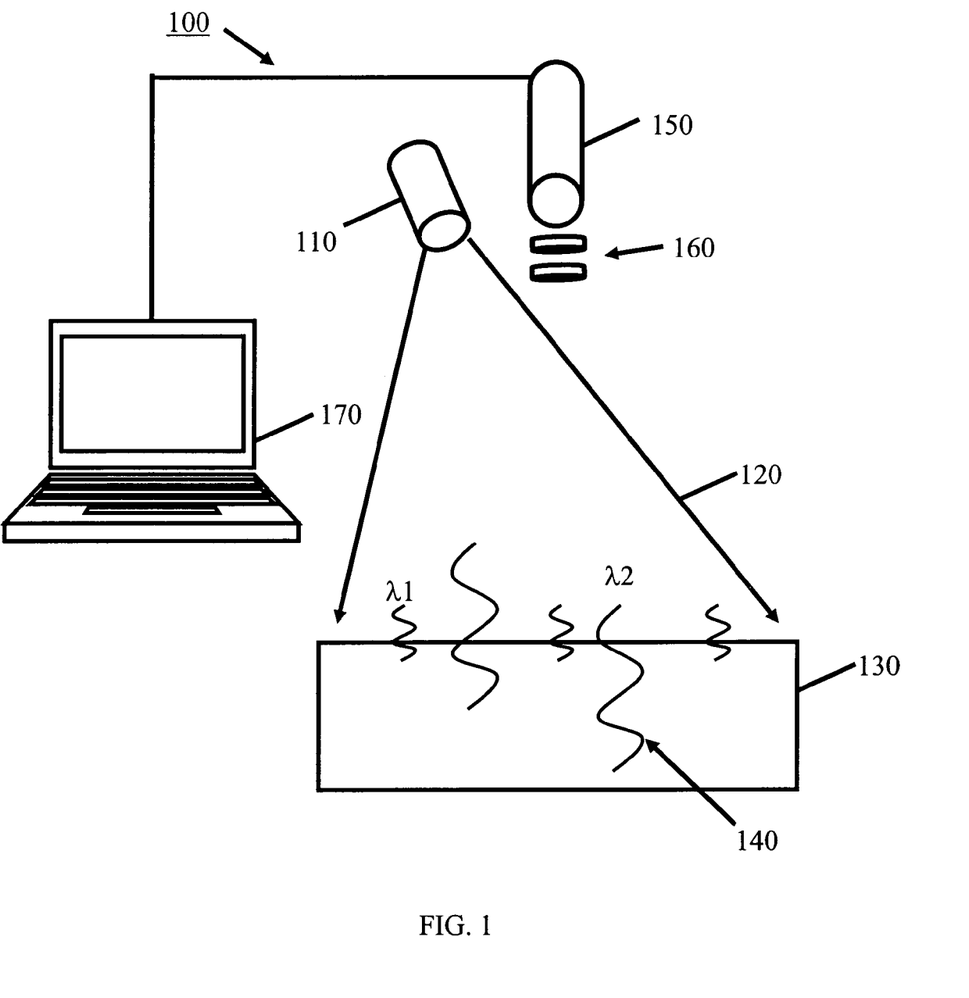
FIG. 1 is a block diagram illustrating the excitation of luminescence of different wavelengths in a solar cell.

FIG. 1 illustrates a system 100 comprising at least one excitation source 110 for exciting luminescence that is emitted from a semiconductor structure 130. More particularly, in the system 100 of FIG. 1, the excitation source 110 is one or more light sources emitting light 120 incident on at least one surface of the semiconductor structure 130. However, as described hereinafter, other types of excitation sources may be practiced, including electrical sources (e.g., a voltage or current source), or a combination of light and electrical sources. The semiconductor structure may be a bare wafer (e.g., an unprocessed silicon sample, a partially processed or fabricated semiconductor device, or a fully processed or fabricated semiconductor device). More preferably, the semiconductor structure may be a bare wafer, a partially fabricated solar cell, or a fully fabricated solar cell.

In this embodiment of the invention, the light source 110 generates light suitable for inducing luminescence (i.e., photoluminescence, or photoluminescence excited simultaneously with electroluminescence excited by an electrical source) in silicon and is used to illuminate the silicon sample. For example, monochromatic or substantially monochromatic light (e.g. from a laser) or partly filtered light from a broad spectrum light source (e.g. a flash lamp) may be used to illuminate the silicon sample. Light sources 110 that can be practiced comprise one or more lasers, a broad spectrum light source combined with suitable filtering to provide partly filtered light, and an array of light emitting diodes (LED). Other light sources may be practiced without departing from the scope and spirit of the invention.

The solar cell 130 emits luminescence 140 from its surface of differing wavelengths $\lambda 1$, $\lambda 2$ where $\lambda 1 < \lambda 2$. The luminescence emitted of shortest wavelength $\lambda 1$ is generated closer to the surface that light 120 is incident upon, while luminescence of longer wavelength $\lambda 2$ can be generated deeper in the solar cell than from that surface.

Also as shown in FIG. 1, the system 100 comprises a luminescence capture device 150, at least one filter 160, and a computing device 170, with which the embodiments of the invention may be practiced. Filtering is applied to the generated luminescence to greatly reduce the spectral content of the luminescence above or below specified wavelengths or both (for example by using a short pass filter, a long pass filter or a band pass filter, respectively). The filter 160 is illustrated as discrete hardware components in FIG. 1. The at least one filter 160 may implemented separately or as part of the luminescence capture device 150. While two filter elements 160 in combination are depicted in FIG. 1, it will be appreciated by those skilled in the art that the filtering may be implemented using one or more filter elements. The filtering is applied during capture of the luminescence intensity. In another embodiment of the invention involving spectrum mapping, the at least one filter may be implemented in software executed by the computing device 170.

The filter 160 filters the luminescence excited in the semiconductor structure. The long cutoff wavelength is greater than the short cutoff wavelength. The filtering may be implemented using different filters with different cut off wavelengths. In the embodiment of FIG. 1, the filtering is preferably implemented in at least two separate measurements using at least two short-pass filters, one with a longer cut off wavelength than the other. Alternatively, the filtering may be implemented using a long-pass filter, where the long-pass filtered energy is subtracted from the total spectrum of luminescence. Modifications and/or substitutions may be made to the filter 160 without departing from the scope and spirit of the invention subject to the requirement that luminescence intensities in at least two different spectral intervals are measured separately.

The luminescence induced in the silicon structure is captured with a luminescence capture device 150. In this regard, the embodiments of the invention may be applied to image portions of arbitrary size. Broadly speaking, the determination of diffusion length is based on a comparison of luminescence intensities integrated over different spectral intervals. The method can be carried out: a) spatially resolved, and b) non-spatially resolved. For the spatially resolved cases, an imaging or a mapping technique can be applied. In an imaging technique, the luminescence capture device 150 is an imaging device comprising an array with more than one individual sensor, such as a CCD camera or any other pixel detector. Each pixel collects the luminescence from a limited area on the wafer, thereby creating an image for the entire wafer. In some instances hereinafter, reference may be made simply to the "sensor".

The imaging device may comprise a focusing element and a focal plane array of light-sensitive electronic elements. The focal plane array may be made of silicon and may be cooled. Cooling improves the signal-to-noise ratio of such a focal plane array. The focal plane array of light-sensitive electronic elements may comprise a charge coupled device (CCD) array. However, as described hereinafter, other devices besides a CCD array may be practiced without departing from the scope and spirit of the invention. The imaging device may be used in combination with optical imaging and/or filtering arrangements. For example, the luminescence capture device 150 may be a digital camera having a silicon CCD array and be provided with a digital interface (e.g., USB or Firewire) or storage media (e.g., a DV tape or memory stick) for communication of recorded images. Alternatively, the focal plane array of light sensitive electronic elements may be made from InGaAs. In another embodiment of the invention, rather than generating individual pixels, a number of pixels of an image may be "binned" together to produce a smaller sampling set for further processing as a portion of the captured image of luminescence.

Besides the foregoing, additional Focal Plane Array (FPA) imaging technologies may be practiced, including:
a) Complementary Metal Oxide Semiconductor (CMOS), where the semiconductor is silicon;
b) Hybrid CCD—CMOS Read Out Integrated Circuit (ROIC);
c) Hybrid Silicon PIN—CMOS ROIC; and
d) Hybrid Mercury Cadmium Telluride (HgCdTe or MCT)—CMOS ROIC.

For the purpose of imaging devices, the foregoing FPA imaging technologies a) to d) may be practiced in further embodiments of the invention. In that case, technologies a) to d) above (as well as InGaAs FPA) have the advantage of potentially much higher pixel readout rates and potentially highly flexible sub-image readout. Details of each of these four technologies are set forth hereinafter.

In a standard CCD FPA, light is converted into charge carriers in each pixel. The charge is transferred from all pixels, serially, to a single amplifier at the corner of the array. This is done by first shifting the charge in each row of pixels down one row into the row below. In the case of the lowest row of the imaging array, the "row below" is a horizontal shift register. After each vertical shifting operation, the charge contained in the horizontal shift register is shifted, one pixel at a time, to the right or left. At the end of this register, the charge which is shifted "off" the register is amplified (converted into a voltage). This voltage appears at a connector on the edge of the CCD FPA. Additional electronic circuits buffer and/or amplify the voltage and digitize the voltage. After all the elements of the horizontal shift register have been shifted out and digitized, another vertical shift is performed, loading the horizontal shift register with another row of data. This process is repeated until all pixels have been digitized.

Some large format CCDs (typically multi-megapixel) have an amplifier in each corner, and the vertical/horizontal readout process occurs separately for each quadrant. This allows four times faster readout than in the case of a single amplifier. Other minor variations also exist. The serial readout process of the CCD architecture is inherently slow—for example if the horizontal shift register is clocked at 1 MHz, a 1 megapixel CCD takes about 1 second to read out. There are inherent limits in the charge transfer process that limit the maximum clock speed, and in addition, the high clock speeds typically used mean that the bandwidth of the output amplifier is necessarily high and as a consequence amplifier noise is high. Any mechanism that can amplify and digitize charge from each pixel in either a fully or partially parallel fashion will allow much faster frame rates and/or much lower noise levels.

CMOS sensors (a) are like light sensitive memory chips. Like a CCD, CMOS sensors have a matrix of light sensitive pixels. Unlike in a CCD, the charge from each pixel is converted into a voltage by an amplifier built into each pixel. The "analog" voltage signal in each pixel can be randomly addressed just like in a memory chip. A CMOS sensor typically has several digitizing circuits working in parallel, located physically next to the imaging array, on the same silicon IC. These circuits address different sub-arrays of the matrix, reading out the voltage of each pixel within the sub-array. Because different sub-arrays are digitized in parallel, the overall frame rate can be much higher than in a CCD. Alternatively, (at least in principle) a slower frame rate can be used, with lower noise owing to the low bandwidth that can be used for each digitizing circuit. CMOS FPA technology is evolving rapidly but currently is inferior to CCDs except for frame-rate.

There are some inherent problems with pure CMOS technology and pure CCD technology that are solved by a technology that separates the detector and readout electronics into separate chips, connected together with indium bumps either at each pixel site (fully parallel amplification), or in a partially parallel fashion. Where the detector is silicon, these are known as "hybrid" FPAs to distinguish them from CCDs. Hybridisation (Hybrids using CMOS ROIC) allows a silicon-based FPA with characteristic superior to pure CCD and pure CMOS, since the detector and readout can be separately optimized. This can result in superior sensitivity, noise and speed performance. In the case of InGaAs or HgCdTe detectors, it is understood that these must be connected to a CMOS ROIC at each pixel in the same way (indium bumps) so the term "hybrid" is not often used.

In Hybrid CCD—CMOS ROIC [partially parallel amplification] architecture (b), charge is still shifted in vertical columns in a CCD detector. However, instead of the charge being shifted into a horizontal shift register at the bottom, each column is connected, via an indium bump bond, to a separate amplifier and analog signal processing chain (typically Correlated Double Sampling signal processing) located on the CMOS chip. For a 1024×1024 pixel array, the number of analog signal processing chains is 1024 times as many that in a CCD. These may be operated at very low bandwidth (~kHz) giving similar frame rates as a CCD (with very low noise) or at high speed (~1 to 10 MHz) giving very high frame rates. For full frame read out, frame rates of kHz are possible. For partial frame readout (where only the lower part of the image is read out) frame rates of 10 to 100 kHz are possible. In the low noise case, the number of analog to digital converters (ADCs) between which the 1024 analog signal processing chains are multiplexed is not critical. For high frame rates, a large number of ADCs must exist on the CMOS chip. CMOS ROIC chips exist with 32 ADCs.

Low noise can be combined with fast readout at the expense of resolution. In this mode, as each column is clocked vertically, the charge is accumulated in a "summing pixel" at the bottom of the column, before it is amplified. This "column binning" may be performed at high clock rates (MHz). This mode gives a "linescan" of 1024 separate binned columns. For example, a 1024×1024 array with full column binning has the following characteristics: vertical clock speed=5 MHz, time for binning each column=200 microseconds, and maximum frame rate is therefore 1/(0.0002)=5 kHz. Further information about this technology is available at the URL <http://architect.wwwcomm.com/Uploads/Princeton/Documents/Library/Hybrid_Sensor_Technology.pdf>. In the description at the noted URL, two columns share an amplifier and analog signal processing chain, so there may be 670 such chains for a 1340 column CCD.

In Hybrid Silicon PIN—CMOS ROIC [fully parallel amplification] architecture (c), each detector pixel is a "separate" silicon PIN (p-type/intrinsic/n-type) diode fabricated on a single silicon chip. The separation of each pixel is accomplished by having separate surface electrodes and dopant structures. The silicon is continuous, i.e. nothing separates each pixel inside the silicon chip. The detector chip is mated with a CMOS ROIC chip using the indium bump bond method at each pixel. The CMOS ROIC provides a separate amplifier and analog signal processing chain for each pixel, resulting in an output voltage at each pixel that may be randomly addressed (similar to a memory chip). A large number of ADCs on the CMOS ROIC may separately digitize sub-arrays of the total array, giving very large frame rates. Reducing the region of interest to be read out can further increase the frame rate. This may be highly beneficial for the self-consistent method. For more information about this technology, see the following URL: <http://idtl.stsci.edu/products/publications/spie03/SPIE2003%20San%20Diego-%20HyViSI.pdf>.

Hybrid Mercury Cadmium Telluride (HgCdTe or MCT)—CMOS ROIC technology (d) is similar to (c) above, except the detector is not silicon. The advantage over silicon is that the detection efficiency is high for the whole of the silicon luminescence spectrum.

In a mapping technique, a single detector is used that collects the luminescence from a limited area of the wafer. With a so-called XY stage, the sample and the detection system are moved relative to each other to obtain a map of the luminescence intensity. The luminescence capture device may comprise a mapping tool. One single detector may be used that collects the luminescence from a specific area of the wafer. In still another (non-spatially resolved technique) embodiment of the invention, a large area detector may be used to obtain spatially averaged intensities at different wavelengths to determine an average diffusion length (averaged over the whole of, or a part of, the wafer). Such a large area detector may comprise a Silicon photodiode, a Germanium photodiode, an InGaAs Photodiode or a HgCdTe photodiode, for example.

In photoluminescence and electroluminescence imaging, the information about the intensities in different spectral intervals is achieved by comparison of two measurements with different filtering, which includes the variation where only one measurement is taken with filtering and where the intensity of that measurement is compared to the total intensity measured without filtering. The filtering in that case is carried out during data acquisition. With a single detector, i.e. with non-spatially resolved measurements or with a mapping system, the spectrally resolved luminescence intensity can be measured for instance by passing the luminescence through a monochromator and spectrally scanning the spectrum for each pixel. The measurement with a monochromator can actually also be described as a form of filtering, and again this filtering must be carried out during data acquisition. However, if the spectral information is available, the comparison of the integral intensities from different spectral intervals can be carried out after the data acquisition using computer algorithms.

For photoluminescence and electroluminescence and combinations thereof (i.e. photoluminescence with external bias control), the embodiments of the invention include:
1) Non-spatially-resolved measurements with different filtering;
2) Non-spatially-resolved, spectrally-resolved measurements (for example using a monochromator in combination with a single detector) with subsequent data analysis with integration of the intensity over specific spectral intervals;
3) Spatially-resolved, mapping measurement of each pixel with different filtering;
4) Spatially-resolved, spectrally-resolved mapping measurement (for example using a monochromator in combination with a single detector) with subsequent data analysis with integration of the intensity over specific spectral intervals for each pixel; and
5) Spatially-resolved, non spectrally resolved imaging measurement with different filtering in at least two separate measurements. The same filtering applies to all pixels in a single measurement.
6) Spatially-resolved, spectrally-resolved imaging measurements with individual filtering for each pixel. This variation may be implemented using different filters in front of individual pixels on a CCD (as in color video cameras). The diffusion length may be determined from one single measurement.

While a general-purpose computer is depicted in FIG. 1 as the computing device 170, any computing device capable of processing digital data may be used. Thus, for example, the system maybe implemented with a dedicated microprocessor and associated circuitry, or a handheld computing device such as a PDA. The electronic circuits for digital data processing may also be located on the same microchip as the luminescence capture device. Also, the computing device may be coupled to the luminescence capture device 150 to receive data directly from the luminescence capture device and/or to control the luminescence capture device. Alternatively, the image data from the luminescence capture device may be provided offline to the computing device 170.

In addition to receiving captured images from the luminescence capture device 150, the computer 170 can control operation of the luminescence capture device 150, the at least one filter 160 and the excitation source 110 (the connection to the computer 170 is not shown in FIG. 1). Further details of the computer implementation are described hereinafter.

In the embodiments of the invention, electron-hole pairs are generated close to the surface either by strongly absorbed incident light in the photoluminescence mode or by injection from the contacts at the surface by applying a voltage in the electroluminescence mode or by a combination thereof, i.e. with illumination and electrical injection or extraction of carriers through the contacts. In either case, the minority carriers distribute themselves afterwards by diffusing from the surface into the interior of the cell. If the diffusion length is large, the minority carriers fill the entire semiconductor sample volume almost homogeneously, whereas the minority carriers are located closer to the surface if the diffusion length is small. This difference in the carrier distribution affects the emitted light differently at different wavelengths. Since short wavelength light probes the carrier density close to the surface, there is little difference in the emitted intensity at short wavelength between regions of small or large diffusion length. A larger difference in the emitted intensity between regions of small or large diffusion length is observed for long wavelength light. This light originates from the entire cell if the diffusion length is large, but originates only from close to the surface if the diffusion length is small and is less intense.

The spectrally integrated intensity measured at long wavelength is divided by the spectrally integrated intensity measured at short wavelength. For a large diffusion length, this division results in a large number. For a smaller diffusion length, the division results in a small number. This number is therefore a measure of the diffusion length. Using this division, spatially inhomogeneous excitation conditions in the incident light for the photoluminescence mode or the injection current for the electroluminescence mode drops out, since those conditions affect the emitted light at short and long wavelengths by the same factor. This is an improvement over using the electroluminescence image alone as a diffusion length map. In the latter, the spatial variation of the luminescence intensity across the image is used as a direct measure for the diffusion length. Spatially non-homogeneous excitation conditions, which can result from non-homogeneous illumination in photoluminescence or from non-homogeneous carrier injection in electroluminescence, lead to a misinterpretation of the data. In addition series resistance effects can lead to artificial contrast in a single electroluminescence image that is not related to variations in the diffusion length. Such artificial contrast leads to a misinterpretation of a single electroluminescence image but drops out in the ratio of two measurements taken with identical current injection.

In comparison to existing techniques, the embodiments of the invention do not require some of the additional knowledge (for example information about carrier mobilities generally and about spatial variations of the carrier mobilities specifically, lateral carrier generation variations, lateral series resistance effects) that such techniques require and in some respects is less sensitive to the additional knowledge. Advantageously, the embodiments of the invention are applicable to photoluminescence, electroluminescence, or a combination thereof (i.e. from bare wafers, partially processed solar cells and finished solar cells). Unlike existing techniques, the influence of photon reabsorption and of resistive losses due to lateral current flow is not neglected in the embodiments of the invention. Measurements show that these effects can lead to a dramatic misinterpretation of the signal.

In contrast to existing techniques the embodiments of the invention do not require a separate calibration, are applicable to bare wafers and partially and fully fabricated semiconductor devices (e.g., solar cells), are inherently unaffected by lateral series resistance effects and takes photon reabsorption into account analytically. Compared to existing electroluminescence diffusion-length imaging techniques, the embodiments of the invention are self contained and more accurate.

2. Method of Determining Minority Carrier Diffusion Length

Figure 2:
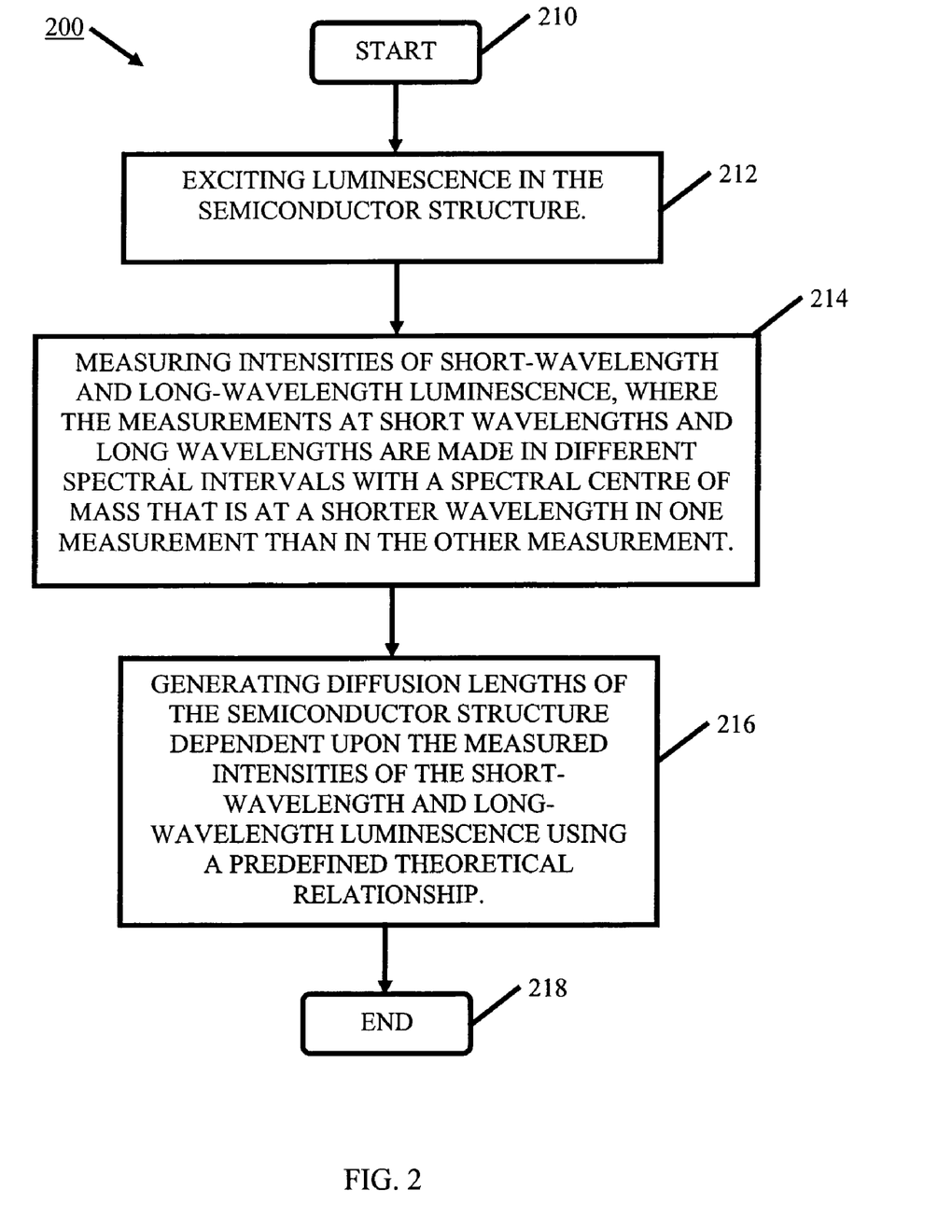
FIG. 2 is a flow diagram illustrating a method of determining minority carrier diffusion length in a semiconductor structure in accordance with an embodiment of the invention.

FIG. 2 illustrates a method 200 of determining minority carrier diffusion length in a semiconductor structure (not shown). Preferably, the semiconductor structure is a bare wafer, or a partially or fully fabricated solar cell. Processing commences in step 210. In step 212, luminescence is excited in the semiconductor structure. The luminescence may be photoluminescence, or electroluminescence, or a combination of the two.

In step 214, intensities of short-wavelength and long-wavelength luminescence are measured. The measurements at short wavelengths and long wavelengths are made in different spectral intervals with a spectral centre of mass that is at a shorter wavelength in one measurement than in the other measurement. The long wavelength is greater than the short wavelength. That is, integral luminescence intensities over two different spectral intervals are measured. This may be done with one single detector, on a pixel-by-pixel basis, or by binning. To obtain the integral luminescence intensity over a specific spectral interval, filtering of the luminescence may be performed. The filtering may be implemented using different filters with different cut off wavelengths. Preferably, the filtering may be implemented using at least two short-pass filters, one with a longer cut off wavelength than the other. Alternatively, the filtering may be implemented using a long-pass filter, where the long-pass filtered energy is subtracted from the total spectrum of luminescence.

In step 216, diffusion lengths of the semiconductor structure are generated dependent upon the measured intensities of the short-wavelength and long-wavelength luminescence using a predefined theoretical relationship. The predefined theoretical relationship is described hereinafter in greater detail under heading 4 ("Relationship Between Intensity Ratio and Diffusion Length"). The diffusion lengths may be generated on a pixel-by-pixel basis, for measurements taken with a single detector, or by binning, for example.

The method described hereinbefore may be applied to photoluminescence or electroluminescence images of bare wafers, or partially or fully fabricated solar cells, or images where both photoluminescence and electroluminescence are combined. The images may be taken using a luminescence capture device such as a FPA, a CCD array or a mapping tool. Such an image may be a pixel-by-pixel measurement of the intensity of the emitted light. Alternatively, binning of pixels may be performed. Short and long wavelength measurements may be made using at least one filter. Preferably, the filtering is implemented using at least two short-pass filters, one with a longer cut off wavelength than the other. Alternatively, the filtering may be implemented using a long-pass filter, where the long-pass filtered intensity is subtracted from the intensity integrated over the total spectrum of luminescence. Division of the measured intensities, combined with an analysis performed only once, yields an image displaying the variation of the diffusion length over the bare wafer, or partially or fully fabricated solar cell. Again, the division may be done pixel by pixel or by binning.

3. Detailed Flow Diagram

Figure 3:
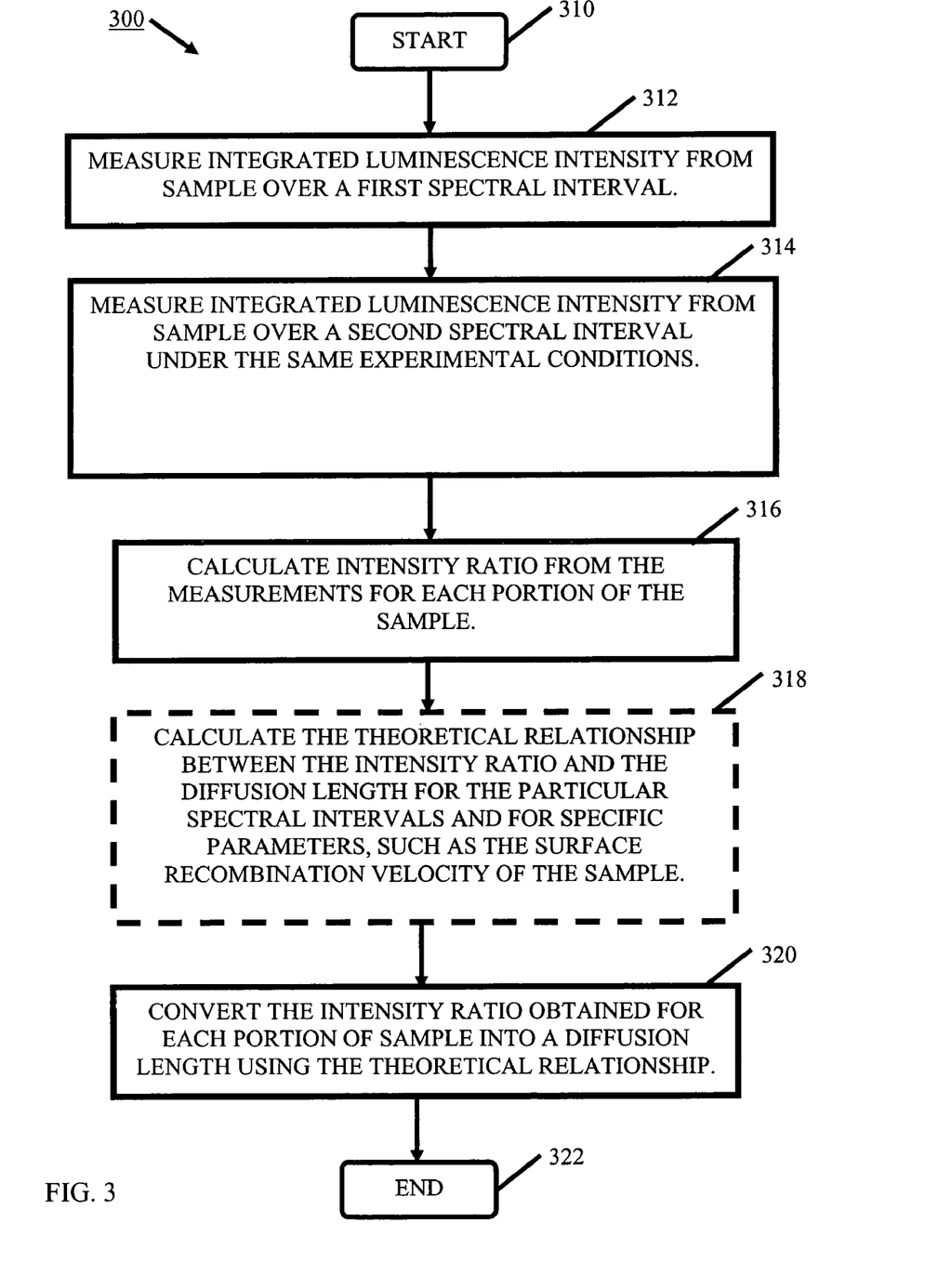
FIG. 3 is a detailed flow diagram illustrating a method of determining minority carrier diffusion length in a semiconductor structure using luminescence.

FIG. 3 illustrates in greater detail a method 300 of determining minority carrier diffusion length in a semiconductor structure in accordance with an embodiment of the invention. Processing commences in step 310. In step 312, the integrated luminescence intensity (e.g. a photoluminescence PL or electroluminescence EL image, or combination thereof) emitted from the semiconductor sample is measured where the luminescence is integrated over a first spectral interval (e.g., using a short-pass filter). The measured intensity may be saved or stored. The data may be captured by a luminescence capture device and transferred to a storage device of a computer, for example. In step 312, if a short-pass filter is used, the filter may have either a short or a long cutoff wavelength. For the purposes of discussion only, the filter may have a short cutoff wavelength. In step 314, luminescence intensity (e.g. a photoluminescence PL or electroluminescence EL image, or combination thereof) is measured over a second spectral interval (e.g., using a short-pass filter). The measured intensities may be saved or stored. Again, the data may be captured by a luminescence capture device and transferred to a storage device of a computer, for example. In one embodiment, images of the luminescence intensities are captured in steps 312 and 314.

In step 314, integrated luminescence intensity from the sample is measured over a second spectral interval under the same experimental conditions. Step 314 is performed under the same experimental conditions as step 312, i.e. with the same position of the semiconductor structure or sample, the same position of the luminescence capture device or camera, the same applied voltage or current (for electroluminescence) or the same illumination conditions (for photoluminescence) or the same voltage or current and the same illumination conditions where both electroluminescence and photoluminescence are used. The order of steps 312 and 314 may be reversed. In step 314, a short-pass filter may be used, which has either a long or a short cutoff wavelength (dependent upon the type of filter in step 312). For the purposes of discussion only, the filter of step 314 has a long cutoff wavelength. In step 316, the intensity ratio is calculated from the measurements for each portion of the sample, which may be a pixel, or a group of pixels for example. The measurements are those obtained in steps 312 and 314.

Step 318 is depicted with broken lines. This is meant to indicate that this step does not need to be performed in any particular sequence in the flow of FIG. 3. For example, it may be performed offline, or it may be performed before steps 312 or 314, or in parallel with steps 312-316, for example. In step 318, the theoretical relationship is calculated between the intensity ratio and the diffusion length for the particular spectral intervals and for specific parameters, such as characteristics of at least one filter, the spectral sensitivity of a sensor, and the surface recombination velocity or velocities of the semiconductor structure or sample. The theoretical relationship is described in greater detail hereinafter. In step 320, the intensity ratio obtained for each portion of the sample is converted into a diffusion length using the theoretical relationship. For example, a look up table of values for the theoretical relationship may be used, or the theoretical-relationship between the diffusion length and the ratio may be parameterized, e.g. using a polynomial fit. In the latter case, the ratio may be directly converted into a diffusion length analytically. Processing terminates in step 322.

In accordance with another embodiment of the invention, a system is provided for determining minority carrier diffusion length in a semiconductor structure, such as a bare wafer, or a partially or fully fabricated solar cell. An excitation source like that of FIG. 1 is used to excite the semiconductor structure to emit luminescence from the semiconductor structure. Again, the luminescence may be photoluminescence, electroluminescence, or a combination of both. A luminescence capture device captures two or more images of luminescence intensities excited in the semiconductor structure. One or more short-pass filters are used for filtering at short and long cutoff wavelengths the luminescence excited in the semiconductor structure, where the long cutoff wavelength is greater than the short cutoff wavelength. The short-pass filters are disposed between the semiconductor structure and the luminescence capture device. As described hereinbefore, other filtering arrangements may be practiced. A computing device calculates intensity ratios from captured images of luminescence intensities dependent upon short-wavelength and long-wavelength intensities from corresponding portions of the captured images, and converts the intensity ratios into diffusion lengths using a theoretical relationship dependent upon characteristics of the short-pass filters the spectral sensitivity of a sensor, and surface recombination velocity or velocities of the semiconductor structure.

Operations of the computing device are performed as a spatially averaged quantity using a single detector, on a pixel-by-pixel basis, or by binning, for calculating the intensity ratios and converting the intensity ratios into diffusion lengths. The system may further comprise a computing device for calculating the theoretical relationship between the intensity ratios and the diffusion lengths dependent upon the short-pass filter characteristics, the spectral sensitivity of a sensor, and the surface recombination velocity or velocities of the semiconductor structure.

4. Relationship between Intensity Ratio and Diffusion Length

The influence of the minority carrier distribution on the spectrum of luminescence of bare wafers, or partially or fully fabricated solar cells is described hereinafter. Due to re-absorption of emitted radiation within a bare wafer, or a partially or fully fabricated solar cell, an inhomogeneous carrier distribution is reflected differently in the emitted spectrum that escapes the device in different wavelength ranges. In the embodiments of the invention, the measurement of minority carrier diffusion length involves taking the ratio of luminescence intensities measured in different wavelength ranges. A direct correlation exists between the absolute diffusion length and the luminescence (photoluminescence or electroluminescence or both) intensity ratio between measurements with two different wavelength intervals.

For a quantitative description of the dependence of the emission spectrum on the distribution of the minority carriers, it must be known how carriers injected into the base of a solar cell or that are photogenerated within a silicon sample distribute themselves. For carriers injected electrically into a solar cell this relationship can be described analytically as described below. For photogeneration of carriers in photoluminescence experiments, the carrier distribution must be calculated numerically, for example using one-dimensional device simulation packages. In specific cases, where the photoluminescence excitation is by short wavelength light, the generation of carriers can be approximated by a delta function near the illuminated surface. In that case the analytic relationships to be described below for electroluminescence can also be used for photoluminescence. Then, how this distribution affects the emission spectrum must be found.

4.1 Carrier Distribution

For example, consider the injection of electrons from a pn junction into a p-type base of a solar cell. For an applied voltage $V_{appl}$, the electron distribution across the sample as a function of the distance x from the front surface $n_e(x)$ is given as $$n_e(x) = A\exp\left(\frac{x}{L_e}\right) + B\exp\left(-\frac{x}{L_e}\right), \tag{1}$$

with $$A = n_e(0)\frac{1-r}{1-r+(1+r)\exp\left(\frac{2d}{L_e}\right)} \tag{2}$$

and $$B = n_e(0)\frac{1+r}{1+r+(1-r)\exp\left(-\frac{2d}{L_e}\right)},$$

where $r = S\,L_e/D_e$, and $$n_e(0) = \frac{n_i^2}{N_A}\exp\left(\frac{eV_{appl}}{kT}\right). \tag{3}$$

In Equations (1)-(3), $L_e$ is the diffusion length, $D_e$ is the diffusion coefficient of silicon, S is the surface recombination velocity, $n_i$ is the intrinsic carrier concentration, $N_A$ is the doping concentration, and kT is the thermal energy, x is the distance from the pn junction, $V_{appl}$ is the applied voltage, e is the elementary charge, and d is the thickness of the sample. The surface recombination velocity is assumed to be constant (i.e. not dependent on the carrier concentrations) and the same for the front and the rear surfaces, respectively. For photoluminescence experiments, the carrier distribution must generally be calculated numerically. However, for excitation with short wavelength light, the generation profile is well approximated by a delta function near the illuminated surface and the above analytical approach can be used.

4.2 Photon Emission

Photons with energy $\hbar\omega$ in the energy interval $d\hbar\omega$ are emitted by radiative recombination of electrons and holes at a rate $g_\gamma(x, \hbar\omega)$. The photon current $dj_{y,em}(\hbar\omega)/d\hbar\omega$ emitted through the surface in the energy interval $d\hbar\omega$ follows from integrating the contributions from the generation rate $g_y(x, \hbar\omega)$ of the photons over the thickness of the solar cell after accounting for re-absorption and reflection at the rear ($R_r$) and at the front ($R_f$), where $R_r$ and $R_f$ are the reflectivities of the front and of the rear surfaces, respectively. Any spectral dependence of the reflectivity is neglected in the analysis below but could be included explicitly.

$$\frac{dj_{y,em}}{d\hbar\omega}(\hbar\omega) = [1 - R_f(\hbar\omega)] \int_d^0 \left\{ \begin{array}{c} g_\gamma(x, \hbar\omega) \\ \left[ \begin{array}{c} \exp(-\alpha x) + R_r \\ \exp(-\alpha[2d - x]) \end{array} \right] \end{array} \right\} dx. \quad (4)$$

In Equation (4), $\alpha$ represents the absorption coefficient of silicon.

For non-degenerate electron and hole concentrations, the generation rate $g_y(x, \hbar\omega)$ in Eqn. (4) of photons by radiative recombination via band-band transitions is given in approximation by:

$$g_\gamma(x, \hbar\omega) = \alpha(\hbar\omega)\frac{(\hbar\omega)^2}{4\pi^2\hbar^3 c^2}\exp\left(-\frac{\hbar\omega}{kT}\right)\left(\frac{n_e(x)N_A}{n_i^2}\right), \quad (5)$$

where $\hbar$ and c are Planck's constant and the vacuum speed of light, respectively.

4.3 Detection of Emitted Photons

The photons emitted by the solar cell may be detected by a luminescence capture device (for example a silicon CCD camera) that is not particularly sensitive to the long wavelength radiation emitted by silicon samples. To properly model the intensity detected by the luminescence capture device in combination with at least one specific filter, the luminescence capture device's spectral sensitivity $S_{Capture}(\hbar\omega)$ (the sensitivity of the sensor), including the transmission of its lens, and the spectral transmission $T_{filter}(\hbar\omega)$ of the at least one filter must be included. The spectral transmission of other optical components that are located between the sample and the luminescence capture device, for example one or more additional filters that are required in photoluminescence measurements may be included in the sensitivity $S_{Capture}(\hbar\omega)$:

$$\frac{dj_{y,detect}}{d\hbar\omega}(\hbar\omega) = T_{filter}(\hbar\omega) \cdot S_{Capture}(\hbar\omega) \cdot \frac{dj_{y,em}}{d\hbar\omega}(\hbar\omega) \quad (6)$$

Equations (1)-(3) permit calculating the carrier distribution for a given diffusion length and surface recombination velocity. In photoluminescence experiments, where the generation profile cannot be approximated by a delta function the carrier distribution profile must be calculated numerically. Equation (5) permits calculating the position-dependent spectral photon emission rate, from which the photon flux emitted through the surface is calculated using Eq. (4). Subsequently, Eqn. (6) permits the calculating of the integrated photon flux detected by the luminescence capture device for different filters and as a function of the diffusion length and of the surface recombination velocities. Variation of the diffusion length in this theoretical analysis allows predicting the theoretical relationship between the diffusion length and the intensity ratio obtained with different filters.

The principle of the method to determine the diffusion length is to measure luminescence intensities integrated over different spectral intervals, calculate a ratio of these spectrally integrated intensities and then convert the intensity ratio into a diffusion length using the predefined theoretical relation described above. In the following example calculation for a silicon sample, two measurements with two different short pass filters are assumed, where the transmission of filters is assumed as $T_{filter}=1$ for $\lambda < \lambda_{cut-off}$ and $T_{filter}=0$ for longer wavelengths $\lambda \geq \lambda_{cut-off}$. The thickness of the silicon sample is 300 μm and an applied voltage of 0.6 V is used for the calculation. The sensitivity of the luminescence capture device (in this case a silicon CCD camera) used was taken from the CCD camera's data sheet. Front and rear reflectances, respectively, of the wafer are assumed to be constant over the wavelength range considered in this example.

Figure 4:
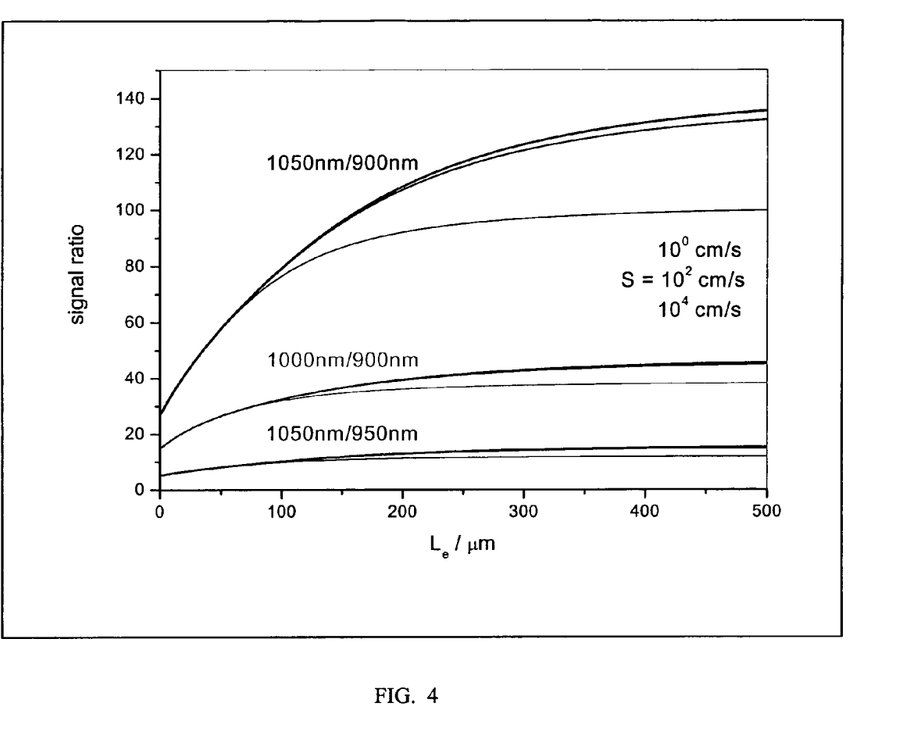
FIG. 4 is a plot of the ratio of luminescence intensities, each measured with a different pair of short-pass filters.

FIG. 4 is a graph plotting ratios of two luminescence intensities, each measured with a different short-pass filter, as calculated according to the theoretical analysis described above. The cut-off wavelengths $\lambda_{cut-off}$ for the filters are indicated in the plot. Results for the signal ratio for each filter combination are shown for three different surface recombination velocities S. For example, the uppermost three curves represent the theoretically predicted intensity ratio of two luminescence measurements as a function of the diffusion length, where one measurement is carried out with a $\lambda_{cut-off}=1050$ nm short pass filter and the second one with a $\lambda_{cut-off}=900$ nm short pass filter. In this group of curves, the top, middle and bottom curves represent the theoretically predicted ratio for different values of the surface recombination velocity (S=0 cm/s, S=100 cm/s and S=10.000 cm/s, from top to bottom, respectively). The other groups of curves show the corresponding theoretical data for different short pass filter combinations as indicated by the labels next to the curves in the plot.

The graph of FIG. 4 shows that if the surface recombination velocity is known with reasonable accuracy, the intensity ratio obtained with a given pair of filters is directly related to the diffusion length. The theoretical curves of FIG. 4 can be used to convert intensity ratios for each pixel into diffusion lengths ($L_e/\mu m$). The calculations show that the curves are relatively flat towards high diffusion length and that the curves calculated for high surface recombination velocities are flatter than those calculated for low surface recombination velocities. The accuracy of the method is correspondingly low in these cases, because a very small variation or experimental error in the intensity ratio corresponds to a large error in the determined diffusion length. For very large surface recombination velocities and long minority carrier effective lifetimes (i.e. long diffusion lengths), the reason for the flat relationship between the intensity ratio and the diffusion length is that the relative carrier profile within the sample is almost unaffected by the bulk diffusion length. The carrier transport is then limited by diffusion from the front to the rear surface and approaches a linear relationship with close to zero carrier density near the rear surface regardless of the bulk diffusion length.

Experimentally a situation is desirable where a variation of the diffusion length results in a large variation in the intensity ratio. Given this prerequisite, FIG. 4 shows that the combination of a 1050 nm short pass filter and a 900 nm short pass filter is better than the two other two filter combinations shown in FIG. 4.

In one embodiment, the values of the various theoretical curves (e.g. the ones shown in FIG. 4) may be stored in a lookup table (LUT) in a storage device such as random access memory, a disk drive, or the like, which can be accessed by a processor of the computing device for converting the intensity ratios into diffusion lengths. Alternatively, the theoretical relationship between the intensity ratio and the diffusion length can be fitted with an analytical expression that can be used to analytically convert measured intensity ratios into diffusion lengths.

A small number of embodiments of the invention regarding methods, apparatuses, and systems for determining minority carrier diffusion length in a semiconductor structure have been described. In the light of the foregoing, it will be apparent to those skilled in the art in the light of this disclosure that various modifications and/or substitutions may be made without departing from the scope and spirit of the invention.

We claim:

1. A method of determining minority carrier diffusion properties in a semiconductor material, said method comprising the steps of:
    (a) exciting luminescence in said semiconductor material;
    (b) measuring first and second resulting luminescence signals from said semiconductor material, said first and second resulting luminescence signals having differing wavelength profiles; and
    (c) comparing differences in said first and second resulting luminescence signals to determine said minority carrier diffusion properties in said semiconductor material.

2. A method according to claim 1, wherein the wavelength profile of said first resulting luminescence signal is derived from measuring short wavelength luminescence and the wavelength profile of said second resulting luminescence signal is derived from measuring long wavelength luminescence, said measurements at short wavelengths and long wavelengths being made in different spectral intervals with a spectral centre of mass that is at a shorter wavelength in one measurement than in the other measurement, said long wavelength being greater than said short wavelength.

3. A method according to claim 1, wherein said step (c) further comprises:
    generating diffusion lengths of said semiconductor material dependent upon measured intensities of said first and second resulting luminescence signals using a predefined theoretical relationship.

4. A method according to claim 2, further comprising the step of filtering at short and long cutoff wavelengths said luminescence excited in said semiconductor material, said long cutoff wavelength being greater than said short cutoff wavelength.

5. A method according to claim 4, wherein said filtering is implemented using a long-pass filter, where the long-pass filtered integrated luminescence intensity is subtracted from the total spectrum of luminescence.

6. A method according to claim 3, wherein said generating step comprises the substep of calculating intensity ratios from said measured luminescence intensities.

7. A method according to claim 6, wherein said generating step comprises the substep of converting said intensity ratios into diffusion lengths using a predefined theoretical relationship dependent upon characteristics of at least one filter, spectral sensitivity of a sensor used to measure said luminescence intensities, and surface recombination velocities of said semiconductor material.

8. A method according to claim 3, wherein said theoretical relationship is defined as follows:

$$\frac{dj_{y,detect}}{d\hbar\omega}(\hbar\omega) = T_{filter}(\hbar\omega) \cdot S_{Capture}(\hbar\omega) \cdot \frac{dj_{y,em}}{d\hbar\omega}(\hbar\omega)$$

where $S_{capture}$ is the spectral sensitivity of a sensor used to measure said luminescence intensities, $T_{filter}$ is the transmission of a respective filter, and $dj_{y,em}(\hbar\omega)$ is the photon current emitted through a surface of said semiconductor material in the energy interval $d\hbar\omega$, the quantity $dj_{y,em}(\hbar\omega)$ being dependent upon a specific value of diffusion length and a specific value of surface recombination velocities.

9. An apparatus for determining minority carrier diffusion properties in a semiconductor material, said apparatus comprising:
    means for exciting luminescence in said semiconductor material;
    measuring means for measuring first and second resulting luminescence signals from said semiconductor material, said first and second resulting luminescence signals having differing wavelength profiles; and
    means for comparing said first and second resulting luminescence signals to determine minority carrier diffusion properties of said semiconductor material.

10. An apparatus according to claim 9, wherein said measuring means measures intensities of short-wavelength and long-wavelength luminescence, said measurements at short wavelengths and long wavelengths being made in different spectral intervals with a spectral centre of mass that is at a shorter wavelength in one measurement than in the other measurement, said long wavelength being greater than said short wavelength; and
    said apparatus further comprises means for generating diffusion lengths of said semiconductor material dependent upon measured intensities of said short-wavelength and long-wavelength luminescence using a predefined theoretical relationship.

11. An apparatus according to claim 10, wherein said intensities of luminescence are measured and said diffusion lengths are generated as a spatially averaged quantity using a single detector, or on a pixel-by-pixel basis, or by binning.

12. An apparatus according to claim 10, further comprising means for filtering at short and long cutoff wavelengths said luminescence excited in said semiconductor material, said long cutoff wavelength being greater than said short cutoff wavelength.

13. An apparatus according to claim 10, wherein said generating means comprises means for calculating intensity ratios from said measured luminescence intensities.

14. An apparatus according to claim 13, wherein said generating means comprises means for converting said intensity ratios into diffusion lengths using a predefined theoretical relationship dependent upon characteristics of at least one filter, spectral sensitivity of a sensor used to measure said luminescence intensities, and surface recombination velocities of said semiconductor material.

15. An apparatus according to claim 14, further comprising means for calculating said theoretical relationship between said intensity ratios and said diffusion lengths.

16. A method for determining minority carrier diffusion length in a semiconductor material, said method comprising the steps of:
- exciting said semiconductor material to emit luminescence, said luminescence comprising photoluminescence, electroluminescence, or both;
- filtering said luminescence excited in said semiconductor material at short wavelengths and long wavelengths, each with a spectral centre of mass at a different wavelength;
- capturing luminescence intensities from said semiconductor material, each in a different spectral interval; and
- calculating intensity ratios from said captured luminescence intensities in said different spectral intervals from corresponding portions of said semiconductor material.

17. A method according to claim 16, further comprising the step of converting said intensity ratios into diffusion lengths using a theoretical relationship dependent upon said filtering, spectral sensitivity of a sensor used to measure said luminescence intensities, and surface recombination velocities of said semiconductor material.

18. A method according to claim 16, wherein said semiconductor material is illuminated to produce photoluminescence.

* * * * *